US011707324B2

(12) United States Patent
Hobeika et al.

(10) Patent No.: US 11,707,324 B2
(45) Date of Patent: Jul. 25, 2023

(54) SPINAL CORRECTION ROD IMPLANT MANUFACTURING PROCESS PART

(71) Applicants: SPINOLOGICS INC., Montréal (CA); EOS IMAGING, Paris (FR)

(72) Inventors: Joe Hobeika, Paris (FR); David Invernizzi, Besançon (FR); Julien Clin, Montréal (CA)

(73) Assignees: SPINOLOGICS INC., Montréal (FR); EOS IMAGING, Paris (FR)

( * ) Notice: Subject to any disclaimer, the term of this patent is extended or adjusted under 35 U.S.C. 154(b) by 549 days.

(21) Appl. No.: 16/643,286

(22) PCT Filed: Sep. 1, 2017

(86) PCT No.: PCT/IB2017/001163
§ 371 (c)(1),
(2) Date: Feb. 28, 2020

(87) PCT Pub. No.: WO2019/043426
PCT Pub. Date: Mar. 7, 2019

(65) Prior Publication Data
US 2020/0345420 A1 Nov. 5, 2020

(51) Int. Cl.
*A61B 34/10* (2016.01)
*A61B 17/70* (2006.01)
(Continued)

(52) U.S. Cl.
CPC .......... *A61B 34/10* (2016.02); *A61B 17/7002* (2013.01); *A61F 2/442* (2013.01);
(Continued)

(58) Field of Classification Search
CPC .......... A61B 17/7002; A61B 2017/568; A61B 2034/104; A61B 2034/105;
(Continued)

(56) References Cited

U.S. PATENT DOCUMENTS 10,318,655 B2 * 6/2019 Mosnier ................. A61B 34/10
10,420,615 B1 * 9/2019 Mosnier ............. A61B 17/7011
(Continued)

FOREIGN PATENT DOCUMENTS

JP 2016-093497 A 5/2016
JP 2016-540610 A 12/2016

OTHER PUBLICATIONS

Noshchenko et al., "Evaluation of spinal instrumentation rod bending characteristics for In-Situ contouring," Published online May 11, 2011 in Wiley Online Library (wileyonlinelibrary.com). DOI: 10.1002/jbm.b.31837 (Year: 2011).*

(Continued)

*Primary Examiner* — Sing-Wai Wu
(74) *Attorney, Agent, or Firm* — Nixon & Vanderhye

(57) ABSTRACT

A spinal correction rod implant manufacturing process includes: estimating a targeted spinal correction rod implant shape based on a patient specific spine shape correction and including spine 3D modeling, one or more simulation loops each including: first simulating an intermediate spinal correction rod implant shape from modeling mechanical interaction between the patient specific spine and: either, for the first simulation, the implant shape, or, for subsequent simulation, if any, an overbent implant shape resulting from the previous simulation loop, a second simulation of an implant shape overbending applied to the targeted spinal correction rod implant shape producing an overbent spinal correction rod implant shape representing a difference between: either, for the first loop, the targeted spinal correction rod implant shape, or, for subsequent loop, if any, the overbent spinal correction rod implant shape resulting from the previous simulation loop, and the intermediate spinal correction rod implant shape.

31 Claims, 11 Drawing Sheets

(51) Int. Cl.
  *A61B 17/56*  (2006.01)
  *A61F 2/44*  (2006.01)
  *A61B 17/00*  (2006.01)

(52) U.S. Cl.
  CPC ............ *A61B 2017/00526* (2013.01); *A61B 2017/568* (2013.01); *A61B 2034/104* (2016.02); *A61B 2034/105* (2016.02); *A61B 2034/108* (2016.02)

(58) Field of Classification Search
  CPC ............ A61B 2034/108; A61B 34/10; A61B 2017/00526; A61F 2/442
  See application file for complete search history.

(56) References Cited

U.S. PATENT DOCUMENTS

| | | | |
|---|---|---|---|
| 2005/0262911 A1 | 12/2005 | Dankowicz et al. | |
| 2010/0262975 A1* | 10/2010 | Reysa | G06F 9/5077 718/105 |
| 2013/0345757 A1 | 12/2013 | Stad | |
| 2017/0135706 A1 | 5/2017 | Frey et al. | |

OTHER PUBLICATIONS

Stokes et al., "Measurement of a spinal motion segment stiffness matrix," Journal of Biomechanics 35 (2002) 517-521 (Year: 2002).*

Tadanoi et al., "Computer simulation of idiopathic scoliosis initiated by local asymmetric growth force in a vertebral body," Transaction on Biomedicine and Health, vol. 2, 1995 WIT Press, p. 369-376 (Year: 1995).*

International Search Report and Written Opinion, dated May 23, 2018, from corresponding PCT application No. PCT/IB2017/001163.

Noshchenko et al., "Evaluation of spinal instrumentation rod bending characteristics for in-situ contouring", Journal of Biomedical Materials Research, vol. 98B, Issue 1, Jul. 2011, pp. 192-200.

Stokes et al., "Measurement of a spinal motion segment stiffness matrix", Journal of Biomechanics, vol. 35, 2002, pp. 517-521.

Tadano et al., "Computer simulation of idiopathic scoliosis initiated by local asymmetric growth force in a vertebral body", Transactions on Biomedicine and Health, vol. 2, 1995, pp. 369-376.

* cited by examiner

Construction of the finite element model of the patient

Calibrated Biplanar EOS X-Rays

3D Geometry (StereEOS)

Mechanical Finite Element Model: allows computing the forces occurring in the spine when the spine deforms itself, or the deformations of the spine when external forces are applied on it.

A simulation substracting the gravitational forces is done to compute the zero-g geometry of the spine = geometry of the spine when the patient is lying on the operation table intra-operatively

Computation of the target post-op geometry

FIG. 8A

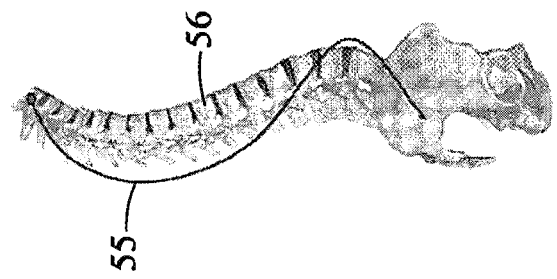

FIG. 8B

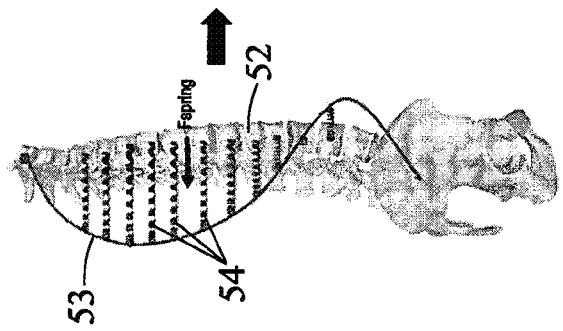

FIG. 8C

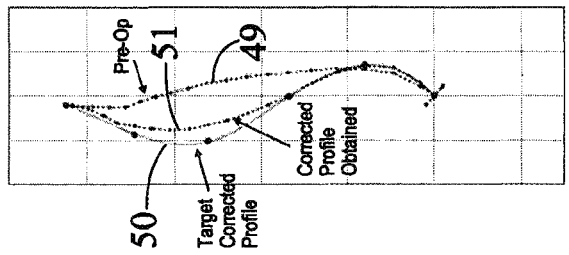

A simplified and quick simulation process using schematic corrective springs is used to allow the user defining a target post-op profile. The biomechanical model makes sure that the target profile is attainable and physiological and that the forces required to obtain it are safe.
Based on this target post-op profile, a target rod shape is defined.

A simplified and quick simulation process using schematic corrective springs is used to allow the user defining a target post-op profile. The biomechanical model makes sure that the target profile is attainable and physiological and that the forces required to obtain it are safe.
Based on this target post-op profile, a target rod shape is defined.

Refined Simulation Process: Computation of the Rod Deformation during Surgery
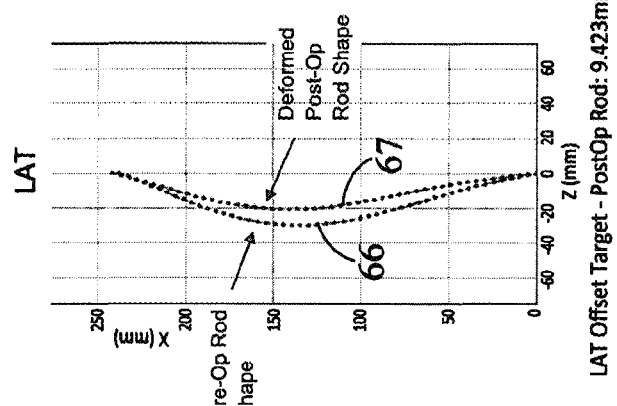
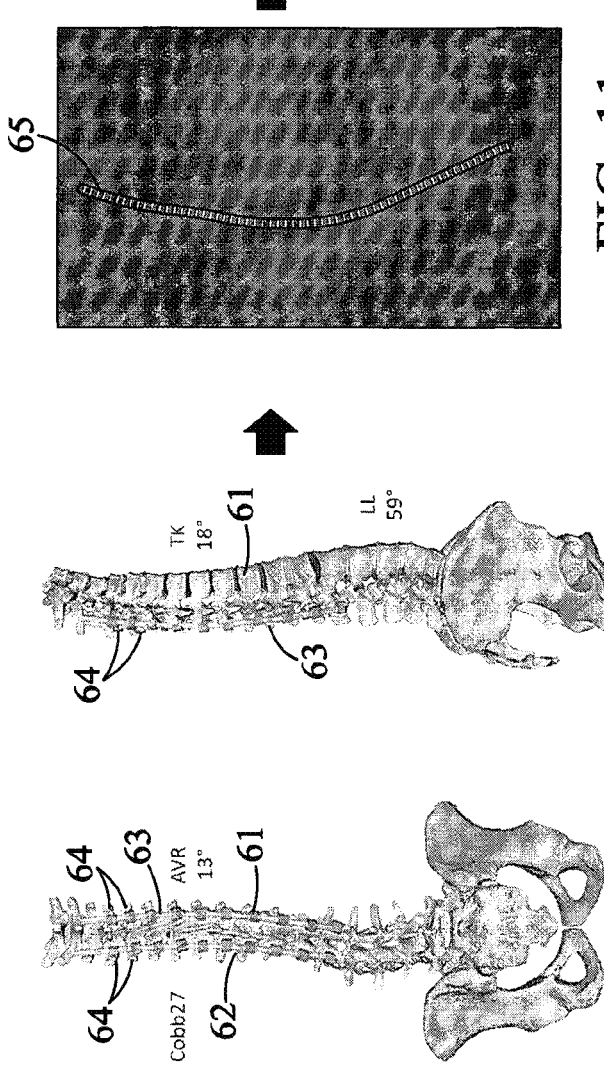
FIG. 10A  FIG. 10B  FIG. 11  FIG. 12
Once the target rod shape has been defined, a refined and more complex simulation process is used to simulate the installation of the rod on the patient (we mimick the surgery). Based on this simulation the deformation of the rod during the surgery is assessed.

The following figures presents the results of the first step (installation of rod):

LAT Offset Target - PostOp Rod: 9.423mm   PA Offset Target - PostOp Rod: 7.51 mm The following figures presents the results of the method applied to process the over-bended rod :

LAT

LAT Offset Target - PostOp Rod: 1.423mm

PA

PA Offset Target - PostOp Rod: 8.808 mm

Legend: Targed / Over-Bended Rod / Post-Op Rod

This figure demonstrates that the over-bended methodology provides a concave rod shape which enables to get the target spine profile.

SPINAL CORRECTION ROD IMPLANT MANUFACTURING PROCESS PART

FIELD OF THE INVENTION

The invention relates to spinal correction rod implant manufacturing process part methods determining the spinal correction rod implant to be manufactured and to associated spinal correction rod implant manufacturing processes manufacturing said determined spinal correction rod implant.

This determined spinal correction rod implant, once manufactured and implanted on patient spine, will help correcting, at least in part, a spine of a patient suffering from scoliosis.

BACKGROUND OF THE INVENTION

According to a first prior art, it is known to manufacture a generic spinal correction rod implant that is delivered to the surgeon who will twist the generic spinal correction rod implant within surgery operating room so as to get at a patient specific spinal correction rod implant, most often based on a paper sheet containing a set of patient specific numerical values. Such twisted patient specific spinal correction rod implant may then be implanted on said patient vertebral spine.

In this first prior art, it is known that the planned spinal correction rod implants are usually bent by the huge forces of muscles reactions during the surgery, and usually the final shape of the implanted spinal correction rod implants in the patient are different from the planned ones. To correct this problem, some surgeons try to apply an overbending to the spinal correction rod implant compared to the surgery planning in order to get a final shape of the implanted spinal correction rod implant in the patient closer to the planning. This overbending applied by surgeons is mainly based on experience and feeling.

In this first prior art, when implanted on patient spine, the mechanical interaction between implanted patient specific spinal correction rod implant and patient spine makes the shape of the patient specific spinal correction rod implant quite different from the one expected, because this mechanical interaction had not been anticipated. Therefore, the patient specific spinal correction rod implant must be taken out, then twisted again, and afterwards implanted again, and this process may be repeated if needed, so as to better match the objective determined in advance by the surgeon.

A first drawback of such first prior art consists in the need to perform many delicate steps the D-day within the surgery operating room, so as to change the generic spinal correction rod implant into a patient specific spinal correction rod implant.

A second drawback of such first prior art consists in the need to perform some excess steps directly on patient spine the D-day within the surgery operating room, so as to change the generic spinal correction rod implant into a patient specific spinal correction rod implant that meets the objective, that is to say that more accurately corresponds to the ideally scheduled patient specific spinal correction rod implant when implanted and when balanced after having undergone mechanical interaction with patient spine because of efforts and pressure exerted by the patient spine on the originally implanted spinal correction rod implant.

According to a second prior art, it is known to manufacture a generic spinal correction rod implant that is delivered to the surgeon who will twist the generic spinal correction rod implant within surgery operating room so as to get at an overbent patient specific spinal correction rod implant, in order to anticipate the efforts and pressure exerted by the patient spine on the patient specific spinal correction rod implant once it is implanted on the patient spine.

In this second prior art, when implanted on patient spine, the mechanical interaction between implanted patient specific spinal correction rod implant and patient spine is often not exactly as scheduled, even if it had been anticipated. Therefore, the patient specific spinal correction rod implant must be taken out, then twisted again a little bit, and afterwards implanted again, and this process may be repeated if needed, so as to better match the objective determined in advance by the surgeon.

A first drawback of such first prior art consists in the need to perform many delicate steps the D-day within the surgery operating room, so as to change the generic spinal correction rod implant into a patient specific spinal correction rod implant.

A second drawback of such first prior art consists either in the need to perform some excess steps directly on patient spine the D-day within the surgery operating room, so as to change the generic spinal correction rod implant into a patient specific spinal correction rod implant that meets the objective, or in the need to require a very skilled surgeon who has so much experience and who is so skilled that he can anticipate precisely the patient specific overbent spinal correction rod implant, such outmost skilled surgeons being rare famous professors.

SUMMARY OF THE INVENTION

The object of the present invention is to alleviate at least partly the above mentioned drawbacks.

More particularly, the invention aims to anticipate, before surgery in the surgery operating room, the required overbending of the patient specific spinal correction rod implant, so that this patient specific spinal correction rod implant, once implanted on said patient spine and once submitted to efforts and pressure exerted by the patient spine, corresponds, in its final state, much more closely, to the shape of implanted patient specific spinal correction rod implant scheduled by surgeon, so as to limit and reduce drastically the numbers of steps to be performed by surgeon in situ, in surgery operating room, in order to take into account the efforts and pressure exerted by patient spine on patient specific implanted spinal correction rod implant.

The invention aims at providing a spinal correction rod implant overbent in advance, that once implanted on patient spine by surgeon, and once undergoing counter efforts and counter pressure by patient spine as a reaction to its deformation by implanted spinal correction rod implant, will get a final shape close or even very close to the scheduled final implanted spinal correction rod implant which is indeed the targeted spinal correction rod implant shape.

The invention aims at providing a conception part of a spinal correction rod implant manufacturing process which will simulate a shape of a patient specific overbent spinal correction rod implant that once implanted and submitted to counter efforts and pressure of patient spine itself deformed by this implanted spinal correction rod implant, will result in a final shape of implanted spinal correction rod implant close or very close to the targeted spinal correction rod implant shape, thereby drastically reducing first the number of steps performed in situ by surgeon and second the skill level of the surgeon required so as to guess the overbending to be applied only out of his or her experienced feeling.

This object is achieved with a spinal correction rod implant manufacturing process part comprising: an estimation step of a targeted spinal correction rod implant shape which is based on a patient specific spine shape correction and which includes a patient specific spine 3D modeling, one or more simulation loops each comprising: a first simulation step of an intermediate spinal correction rod implant shape resulting from a modeling of a mechanical interaction between said patient specific spine and: either, for the first simulation loop, said targeted spinal correction rod implant shape, or, for subsequent simulation loop(s), if any, an overbent spinal correction rod implant shape resulting from the previous simulation loop, a second simulation step of a spinal correction rod implant shape overbending which is applied to said targeted spinal correction rod implant shape to give a resulting overbent spinal correction rod implant shape and which is representative of a difference between: either, for the first simulation loop, said targeted spinal correction rod implant shape, or, for subsequent simulation loop(s), if any, said overbent spinal correction rod implant shape resulting from the previous simulation loop, and said intermediate spinal correction rod implant shape. 3D means tridimensional.

Many complex simulation methods exist, some of them have been experimented by the inventors before reaching the invention, because, at first sight, the simulation of this overbending in order to anticipate the counter action of the patient spine on patient specific spinal correction implant just implanted on said patient spine to deform it, seems to be a delicate and complex mechanical interaction probably requiring sophisticated simulation processes.

On the contrary, the patented simulation process, being part of an implant manufacturing process, is, at the end of the day, a quite simple simulation method, and surprisingly it works, and besides, it works well.

However, for such a simple simulation method to work well, the invention has noticed that the patient specific spine modeling needs to be a precise one, and therefore needs to be a 3D patient specific spine modeling, 2D patient specific spine modeling, even if performed in two or more directions, being insufficient to get at a simulated overbent implant shape which will be close or very close, when manufactured, implanted on patient spine and balanced by deformed patient spine counter efforts, to targeted final implant shape as installed on patient spine.

2D patient specific spine modeling might work, but only with a much more sophisticated simulation method than the one proposed by the invention, and of course corresponding simulation will require much more computing time and take much longer time.

The invention proposes an optimization algorithm which is quite simple, and indeed much simpler than traditional optimization algorithms generally used to tackle such type of mechanical interaction, also practiced before reaching the simpler process proposed by the invention. Indeed, the position of a few key points on the spinal correction rod implant were defined as the optimization variables and optimization algorithms like gradient descent, genetic algorithms and the like, were used to modify the position of these key points so as to find an optimal overbent spinal correction rod implant shape. However, these methods took far too many iterations and lead to very high computational times, indeed probably because, for each iteration, a finite element simulation of the spinal surgery had to be done which generally required between 1 and 2 minutes.

The proposed invention includes a simulation module which enables to add a patient specific biomechanics simulation for the spine and the mechanics interaction with the rod by using a patient specific anatomical simulation of musculo-skeletal spine system including bones (like vertebras), intervertebral discs, muscles and ligaments. The musculo-skeletal simulation planning can simulate the mechanical interactions between the patient's spine and the rods, as the spine induces huge efforts in the rods, the rods are bended and the final shape of implanted rods are slightly different to the shapes planned using only geometrical planning. Thus, by using this simulation planning, it is possible to simulate some specific rods shapes which are overbent compared to purely geometric planning, and these two overbent rods are simulated to get a final spine shape to be very close to the desired geometrical post-operative spine shape.

Preferred embodiments comprise one or more of the following features, which can be taken separately or together, either in partial combination or in full combination.

Preferably, the spinal correction rod implant manufacturing process part comprises only a single simulation loop.

Hence, the process is simpler and quicker, but got accuracy about simulated overbending will end result in a final implanted patient specific spinal correction rod implant which may be only close to targeted patient specific spinal correction rod implant instead of being very close. Process is quicker and simpler but to the cost of reduced accuracy about simulated overbending.

Preferably, the spinal correction rod implant manufacturing process part comprises at least 2 iterative simulation loops, preferably at least 5 iterative simulation loops, more preferably less than 10 iterative simulation loops.

Hence, the process is a bit more complex and a bit longer, but got accuracy about simulated overbending will end result in a final implanted patient specific spinal correction rod implant which will be closer to targeted patient specific spinal correction rod implant. Process is longer and more complex but advantageously leads to increased accuracy about simulated overbending.

Preferably, the number of iterative simulation loops will be determined during running of simulation loops, by checking, at each simulation loop, that the difference between targeted spinal correction rod implant shape and intermediate spinal correction rod implant shape is below a predetermined threshold.

Alternatively, the number of iterative simulation loops is a predetermined number of iterative simulation loops, and wherein preferably said predetermined number of iterative simulation loops depends on the type of patient spine scoliosis and/or on the magnitude of patient spine scoliosis.

Preferably, said mechanical interaction modeling is selected or structured so that, when said resulting overbent spinal correction rod implant is to be implanted on said patient specific spine and when said implanted overbent spinal correction rod implant shape is to be modified by an effective mechanical interaction between said implanted overbent spinal correction rod implant shape and said patient specific spine so as to become an implanted final spinal correction rod implant shape, said implanted final spinal correction rod implant shape is closer to said targeted spinal correction rod implant shape than said intermediate spinal correction rod implant shape from first simulation loop.

Hence, this may help further optimizing a given mechanical interaction modeling so as to make it more accurate, if needed, in its final result leading to a closer implanted final spinal correction rod implant shape to the targeted spinal correction rod implant shape, than would have been an implanted final spinal correction rod implant shape resulting from a direct implantation of the targeted spinal correction rod implant shape.

Several well-known distance minimization methods may be used to determine which one is closer. Advantageously, the least squares distance will be used therefore.

Preferably, said implanted final spinal correction rod implant shape is closer to said targeted spinal correction rod implant shape than said intermediate spinal correction rod implant shape, by at least a factor 2, preferably by at least a factor 5, more preferably by at least a factor 10.

Hence, this may help still further optimizing a given mechanical interaction modeling so as to make it more accurate, if needed, in its final result leading to an implanted final spinal correction rod implant shape even closer to the targeted spinal correction rod implant shape.

Preferably, in said second simulation step, said spinal correction rod implant shape overbending in sagittal plane is the difference between: either, for the first loop, said targeted spinal correction rod implant shape projection in sagittal plane, or, for subsequent loops, an overbent spinal correction rod implant shape resulting from the previous loop projection in sagittal plane, and said intermediate spinal correction rod implant shape projection in sagittal plane.

Hence, accuracy is optimized for the manufactured patient specific overbent spinal correction rod implant shape, at least in the sagittal plane.

Preferably, in said second simulation step, said spinal correction rod implant shape overbending in coronal plane is the difference between: either, for the first loop, said targeted spinal correction rod implant shape projection in coronal plane, or, for subsequent loops, an overbent spinal correction rod implant shape resulting from the previous loop projection in coronal plane, and said intermediate spinal correction rod implant shape projection in coronal plane.

Hence, accuracy is optimized for the manufactured patient specific overbent spinal correction rod implant shape, at least in the coronal plane.

Preferably, in said first simulation step, said mechanical interaction modeling uses, as input parameters, at least both the patient specific spine rigidity before correction and the distances existing between said targeted spinal correction rod implant shape and said patient specific spine before correction.

Hence the mechanical interaction modeling will get at a more precisely simulated counter action of the patient spine over patient specific overbent spinal correction rod implant.

Preferably, in said first simulation step, said mechanical interaction modeling uses, as input parameters, at least both the spinal correction rod implant material and the spinal correction rod implant section.

Hence the mechanical interaction modeling will get at a more precisely simulated effect, on patient specific overbent spinal correction rod implant, of counter action of the patient spine over patient specific overbent spinal correction rod implant.

Preferably, in said first simulation step, said mechanical interaction modeling is based on hybrid model integrating: rigid non-deformable bodies both for patient spine vertebrae and for spinal support implants attached on patient spine vertebrae and supporting said spinal correction rod implant(s), one or more deformable bodies for said spinal correction rod implant(s).

Hence, mechanical interaction modeling is more realistic with respect to simulated mechanical interaction between patient spine and patient specific overbent spinal correction rod implant, and therefore becomes again more precise and leads to a better final result.

Preferably, said hybrid model also integrates: contact interfaces respectively located between rigid non-deformable bodies of spinal support implants and deformable body of said spinal correction rod implant.

Hence, mechanical interaction modeling is still more realistic with respect to simulated mechanical interaction between patient spine and patient specific overbent spinal correction rod implant, and therefore becomes even more precise and leads to an even better final result.

Preferably, said contact interfaces include virtual springs at the nodes where the contact between said two bodies is about to happen, the stiffness of said virtual springs being chosen sufficiently high so as to get only a residual penetration between said two bodies and not too high so as to get a high convergence rate in the iterative resolution process.

Hence, mechanical interaction modeling is still more realistic with respect to simulated mechanical interaction between patient spine and patient specific overbent spinal correction rod implant, and therefore becomes even more precise and leads to an even better final result.

Preferably, the spinal correction rod implant manufacturing process part comprises, after completion of last second simulation step, a supplementary check step including: a phase of simulated implantation of said resulting overbent spinal correction rod implant on said patient specific spine, so as to give an implanted overbent spinal correction rod implant, a phase of modification of said implanted overbent spinal correction rod implant shape by a simulated mechanical interaction between said implanted overbent spinal correction rod implant shape and said patient specific spine so as to give an implanted final spinal correction rod implant shape, a phase of comparison of a first difference between said implanted final spinal correction rod implant shape and said targeted spinal correction rod implant shape with a second difference between said intermediate spinal correction rod implant shape and said targeted spinal correction rod implant shape, a phase of validation checking that said implanted final spinal correction rod implant shape is closer to said targeted spinal correction rod implant shape than said intermediate spinal correction rod implant shape, preferably by at least a factor 2, more preferably by at least a factor 5, even more preferably by at least a factor 10.

Normally, this supplementary check step should not be needed, since the spinal correction rod implant manufacturing process part according to the invention is sufficiently accurate. However, in case of very specific patient spines, or in case two patient spine 3D modeling methods, or in case two mechanical interaction modeling methods, are to be compared for a given patient spine scoliosis specific group, this supplementary check step can help for making the choice. Anyway, it allows to be hundred percent sure of the result, because it allows a direct measure of such result.

Preferably, said estimation step comprises a phase of patient specific 3D geometry modeling, preferably performed at the beginning of said estimation step.

3D patient specific spine modeling is performed as a first sub-step with a patient specific spine 3D geometry modeling. This patient specific spine 3D geometry modeling will increase accuracy of the patient specific spine 3D finite element model. The overbent spinal correction rod implant shape is based on biomechanical finite element simulations patient specific, which means personalized to the patient. These biomechanical simulations anticipate the deformations of the spinal correction rod implant shape during the surgery due to the efforts it undergoes, these efforts mainly coming from the resistance of the patient spine to the correction imposed by the spinal correction rod implant when implanted on patient spine.

Preferably, said 3D geometry modeling phase comprises: a first operation of taking both a frontal and a lateral patient specific spine X-ray images, a second operation of generating a patient specific spine 3D geometry model from both said frontal and lateral patient specific spine X-ray images.

This patient specific spine 3D geometry modeling is simpler, quicker and easier to perform, if based on only two patient specific spine X-ray images presenting different directions, as two frontal and lateral patient specific spine X-ray images. The accuracy of this patient specific spine 3D geometry modeling will still be good, and anyway sufficient.

Preferably, said estimation step comprises: a phase of patient specific spine 3D finite element modeling, preferably performed in the middle of said estimation step.

3D patient specific spine modeling is performed as a second sub-step with a patient specific spine 3D finite element model. Use of a patient specific spine 3D finite element model will improve accuracy of the simulation performed afterwards by the mechanical interaction modeling.

Preferably, said 3D finite element modeling phase comprises: an operation of subtraction of simulated gravitational forces, from a first patient specific spine 3D finite element model, representative of patient spine in vertical image taking position, so as to get a second patient specific spine 3D finite element model, representative of patient spine in horizontal surgery performing position. This specific subtraction simulation phase of an estimation step could also be claimed per se outside the general scope of this invention.

Hence, the second patient specific spine 3D finite element model will lead to more accurate end result than the first patient specific spine 3D finite element model would have, since it corresponds to a more realistic situation, because, during surgery performance, the patient is lying and not standing, the deformation due to patient spine scoliosis being reduced in lying position as compared to standing position.

Preferably, said first patient specific spine 3D finite element model comes from a patient specific spine 3D geometry model.

3D patient specific spine modeling is performed as a second sub-step with a patient specific spine 3D finite element model. The patient specific spine 3D finite element model will be more accurate if based on a patient specific spine 3D geometry modeling.

Preferably, in said 3D finite element modeling phase, said 3D finite element modeling of said patient specific spine includes one or more interbody cages and/or one or more osteotomies.

Hence, this patient specific spine 3D finite element model will be altogether more realistic and more flexible, and will allow taking into account even these "second order" patient spine specificities, thereby still increasing accuracy of end result.

Preferably, said estimation step comprises: a phase of patient specific spine correction feasibility assessment, preferably performed at the end of said estimation step.

Hence, if patient spine scoliosis is too important, and if proposed correction is too important, the proposed correction may be reduced, thereby leading to a not as good end result, but thereby avoiding any risk of damage or breaking of any vertebra of the patient spine due to potentially too high efforts exerted by the patient specific spinal correction rod implant on the patient spine, thereby improving security to the cost of some accuracy loss. This specific feasibility phase of an estimation step could also be claimed per se outside the general scope of this invention.

Preferably, said correction feasibility assessment phase comprises: a first operation of comparison between said second patient specific spine 3D finite element model and an ideally aimed corrected patient spine, so as to get a patient specific spine shape correction and a corresponding targeted spinal correction rod implant, a second operation of feasibility checking of said patient specific spine shape correction, including: checking of biomechanical feasibility, at least by checking that vertebrae of patient specific spine do not interfere with one another when said targeted spinal correction rod implant will be implanted on said patient specific spine, and/or checking of correction feasibility, at least by checking that the corrective forces, exerted when said targeted spinal correction rod implant will be implanted on said patient specific spine, do not exceed a predetermined threshold above which the risk of damage or even of break of a vertebra of the patient specific spine becomes non negligible.

Both biomechanical feasibility and correction feasibility are checked, thereby warranting that scheduled scoliosis correction is altogether first possible and second not dangerous.

Preferably, said second operation of feasibility checking of said patient specific spine shape correction is based on an essentially linear representation of the efforts exerted by said patient specific spine on said targeted spinal correction rod implant.

This essentially linear representation of the efforts exerted by said patient specific spine on said targeted spinal correction rod implant leads to simpler performance while keeping a good level of precision with respect to risk assessment.

Preferably, said essentially linear representation of the efforts exerted by said patient specific spine on said targeted spinal correction rod implant is based on a springs model.

In the process proposed by the invention, this springs model happens to be altogether efficient and simple to implement and to run.

Now several advantageous and specific features about this springs model implementation will be given which lead to more efficient implementation and to more precision in risk assessment.

Preferably, in said springs model, each tensional spring has a first extremity which is attached to the center of a vertebra of the patient specific spine and a second extremity which is attached to the corresponding position of the targeted spinal correction rod implant shape.

Preferably, different existing offsets between vertebrae to be corrected in the patient specific spine, if any, are cancelled so that the initial force applied by the tensional springs on all the vertebrae to be corrected is the same.

Preferably, additional torsional springs are implemented between said targeted spinal correction rod implant shape and said patient specific spine shape so as to correct the axial rotation of the vertebrae of the patient specific spine in the transverse plan with respect to the patient specific spine.

Preferably, different existing offsets between vertebrae to be corrected in the patient specific spine, if any, are cancelled so that the initial moment applied by the torsional springs on all the vertebrae to be corrected is the same.

Preferably, said mechanical interaction modeling uses a stiffness matrix for each intervertebral unit needing a spinal correction in the patient specific spine.

Hence, the obtained compromise between precision of representation and ease of implementation is better.

When patient spine is mentioned, such patient spine may encompass and will preferably encompass not only spine "stricto sensu", but spine and pelvis of the patient.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 8A shows a comparison between examples of patient specific spine lateral profiles, respectively patient spine profile with scoliosis before surgery, the targeted patient spine profile, and the simulated corrected patient spine profile.

FIG. 8B shows schematically a lateral view of an example of a targeted patient spine profile represented with the springs model.

FIG. 8C shows schematically a lateral view of an example of a simulated corrected patient spine profile represented with the springs model.

FIG. 10A shows a frontal view of an example of a 3D representation of an implanted patient spine with the associated implanted spinal correction rod implant shape.

FIG. 10B shows a lateral view of an example of a 3D representation of an implanted patient spine with the associated implanted spinal correction rod implant shape.

FIG. 11 shows a lateral view of an example of a 3D representation of a spinal correction rod implant shape, after implantation on patient spine.

FIG. 12 shows a comparison between two lateral views of two spinal correction rod implant shapes, respectively before implantation on patient spine and after implantation on patient spine, here without overbending.

DETAILED DESCRIPTION OF THE INVENTION

Notably for the detailed description, following definitions will be used, unless stated to the contrary.
- a rod is a spinal rod inserted into spinal implants, like vertebral screws, in order to correct the deformations of the spine of a patient. This rod can have different sections and be made of different materials.
- pre-operatively is a state of the patient, of the rods, and so on, before the surgery, which means before the rod is installed on the patient.
- post-operatively is a state of the patient, of the rods, and so on, after the surgery, which means after the rod is installed on the patient.
- a target rod is the rod's geometry that the spinal surgeon would like to obtain after surgery, which means post-operatively. But, because the rod deforms itself when it is installed on the patient by the surgeon, the goal here is to find the pre-operative rod's geometry, which means before installation, that will lead to the target rod's geometry once installed. The target rod is defined beforehand using a simplified simulation process to define an optimal post-operative geometry of the spine. From this optimal post-operative geometry is computed the target rod's geometry.

pre-operative overbent rod is a rod's geometry (pre-operative) that should lead after installation (post-operative) to the target rod's geometry. The term overbent is used because, typically, to obtain a certain curve post-operatively, the pre-operative rod should present a more important curvature to compensate the deformations it will afterwards undergo during the surgery.

post-operative simulated rod is a rod's geometry obtained once the installation of the pre-operative overbent rod has been simulated. This simulation is done using a personalized biomechanical finite element model of the patient's spine and pelvis, of the spinal implants, screws for instance, and of the rod. The simulation mimics the spinal surgery and, using equations based on the mechanical laws, computes the deformations and forces exerted on the spine and on the rods during the surgery.

Figure 1:
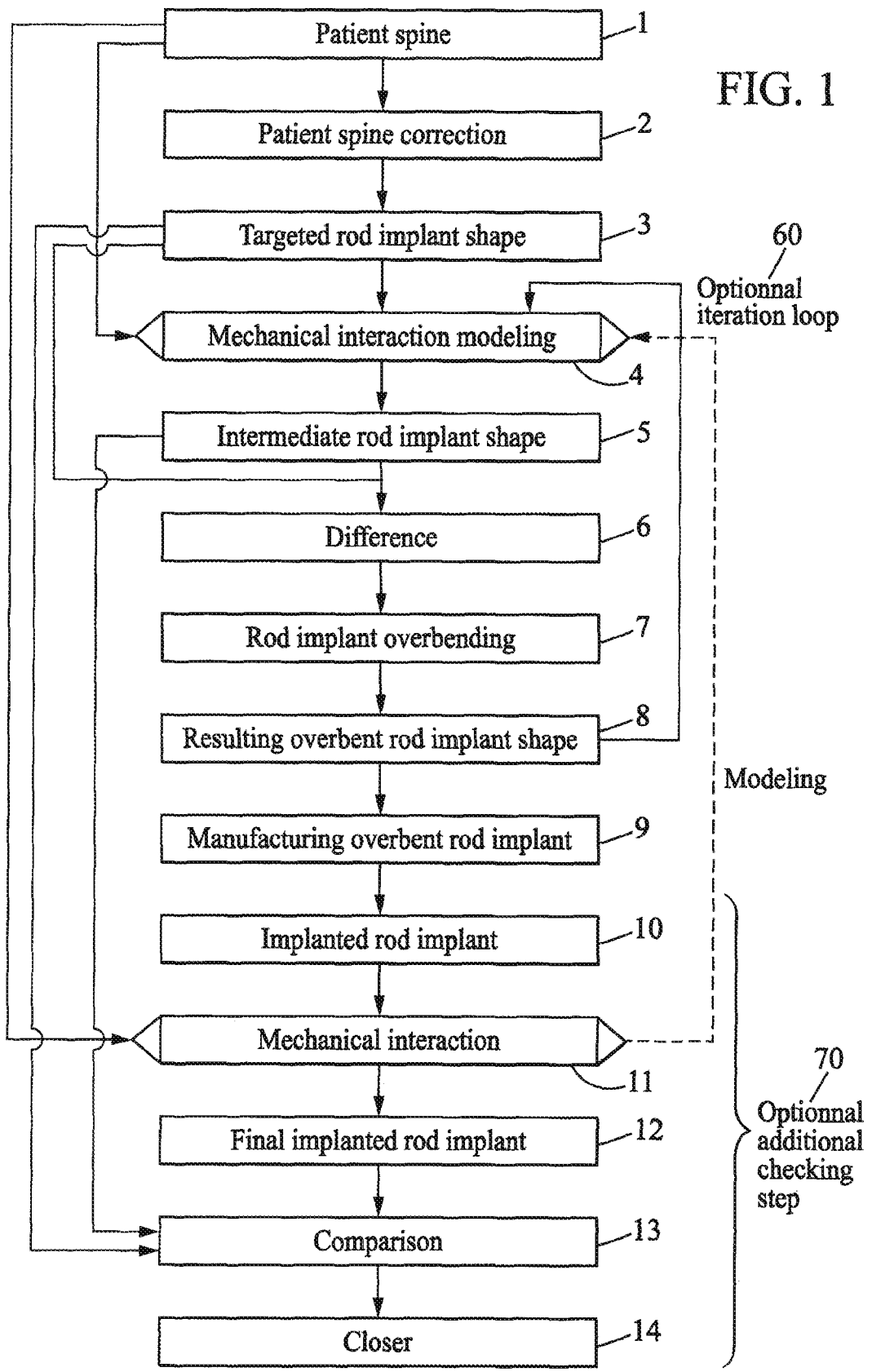
FIG. 1 shows schematically an example of the flow of the main steps of the spinal correction rod implant manufacturing process part according to an embodiment of the invention.

FIG. 1 shows schematically an example of the flow of the main steps of the spinal correction rod implant manufacturing process part according to an embodiment of the invention.

Starting from a patient specific spine 1, a patient specific spine correction 2 is estimated. From the estimated patient specific spine correction 2, a targeted rod implant shape 3 is estimated. From both patient specific spine 1 and estimated targeted rod implant shape 3, a mechanical interaction modeling 4 simulates an intermediate rod implant shape 5. From the estimated targeted rod implant shape 3 and from a simulated intermediate rod implant shape 5, a difference 6 is determined. From determined difference 6, a rod implant overbending 7 is determined. From determined rod implant overbending 7, a resulting overbent rod implant shape 8 is determined. Spinal correction rod implant manufacturing process part according to the invention can end here.

Alternatively, once determined the resulting overbent rod implant shape 8, this determined resulting overbent rod implant shape 8 is injected in the mechanical interaction modeling 4, instead of the targeted rod implant shape 3, so as to give again an intermediate rod implant shape 5, which in turn will give again a difference 6, which in turn will give again a rod implant overbending 7, which in turn will give again a resulting overbent rod implant 8, thereby making another iteration of the simulation loop 60. Spinal correction rod implant manufacturing process part according to the invention can end here, or only after a given number of iterations of this simulation loop 60.

From determined resulting overbent rod implant shape 8, there can be a manufacturing of an overbent rod implant 9 to be implanted on patient spine 1. Alternatively, a representative file or a template of the determined resulting overbent rod implant shape 8 may be edited or manufactured at a first location and then sent at a second location where the real overbent rod implant 8 to be implanted on patient spine 1 will be manufactured therefrom. Spinal correction rod implant manufacturing process according to the invention can end here.

Afterwards, surgery may be performed. Such surgery is not the object of present patent application. The surgeon may implant the manufactured overbent rod implant 9 on patient spine 1, so as to get an implanted rod implant 10. The implanted rod implant 10 may undergo a mechanical interaction 11 with patient spine 1 so as to then become a final implanted rod implant 12. Surgery can end here. Alternatively, measurements may be made on this final implanted rod implant 12, so as to make a comparison 13 with the intermediate rod implant shape 5 from first simulation loop in order to check which one is closer to the targeted rod implant shape 3. Of course, the end result 14 shall be that the final implanted rod implant 12 is closer to the targeted rod implant shape 3 than the intermediate rod implant shape 5 from first simulation loop, and preferably closer by far. Should this not be the case for most of patient spines 1, then the whole process would be pointless. All previous phases 10 to 14 may be alternatively simulated and grouped altogether in an optional additional checking step 70 which would take place after the manufacturing of the overbent rod implant 9 and which simulation is encompassed within the protection sought by filing this invention. The mechanical interaction modeling 4 allows for simulation of the mechanical interaction 11.

Figure 2:
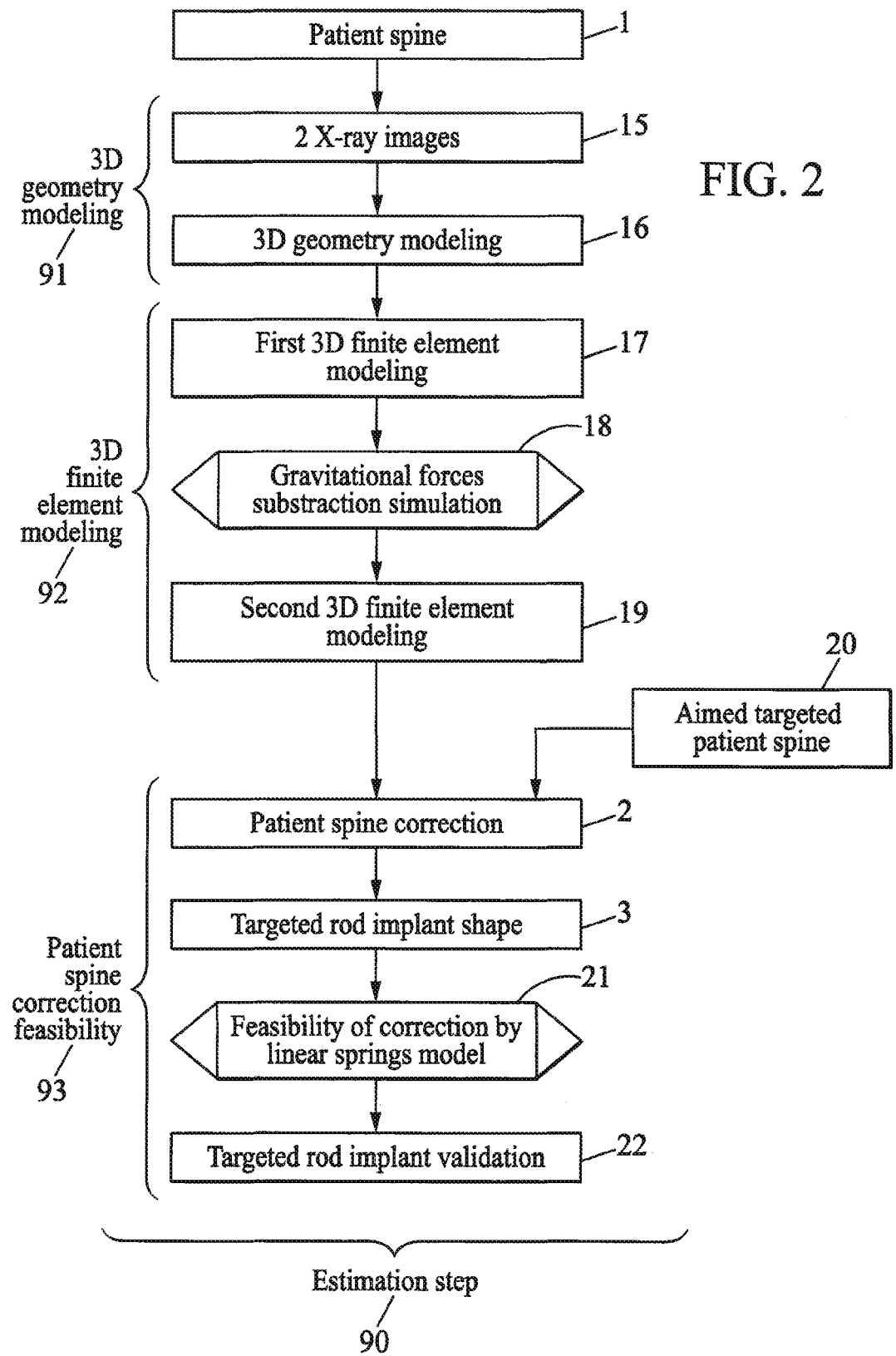
FIG. 2 shows schematically an example of the flow of an estimation step of the spinal correction rod implant manufacturing process part according to an embodiment of the invention.

FIG. 2 shows schematically an example of the flow of an estimation step of the spinal correction rod implant manufacturing process part according to an embodiment of the invention.

Two X-ray images 15 are taken of a patient specific spine 1, of different directions, preferably frontal and lateral images 15. A 3D geometry modeling 16 is made from these two X-ray images 15, preferably using therefor either an existing patient generic 3D geometry modeling or an existing 3D avatar. Both phases 15 and 16 are grouped in a 3D geometry modeling sub-step 91 included in the estimation step 90 represented on FIG. 2.

A first 3D finite element modeling 17 is made from this 3D geometry modeling 16. A phase of gravitational forces subtraction simulation 18 is performed on this first 3D finite element modeling 17 so as to give a second 3D finite element modeling 19. Phases 17 to 19 are grouped in a 3D finite element modeling sub-step 92 included in the estimation step 90.

Both from second 3D finite element modeling 19 and from an aimed targeted patient spine 20, which corresponds to a rather ideal or average spine shape, is estimated a patient spine correction 2. From the estimated patient spine correction 2 is estimated a targeted rod implant shape 3. From the estimated targeted rod implant shape 3, an assessment 21 of the feasibility of correction by a linear springs model is performed. If the feasibility is considered acceptable, then there is a targeted rod implant validation phase 22. If the feasibility is considered not acceptable, then the phase 22 does not validate the targeted rod implant shape 3, and a less ambitious targeted rod implant shape 3 shall be considered by reducing the difference with the original patient spine 1. Phases 2, 3, 21 and 22, are grouped in a patient spine correction feasibility sub-step 92 included in the estimation step 90.

Figure 3:
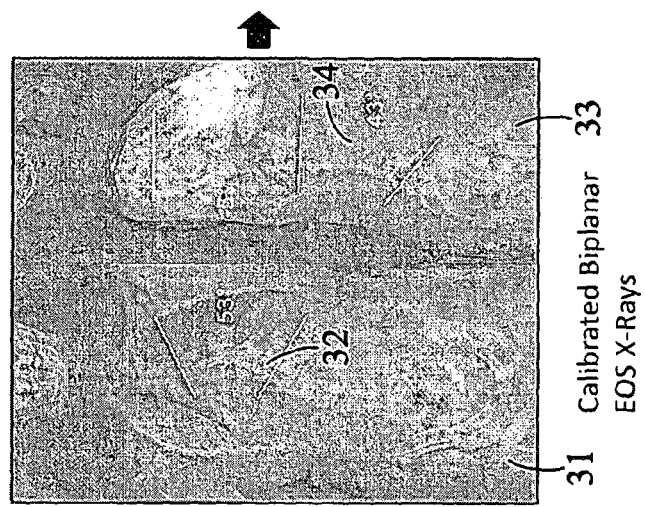
FIG. 3 shows an example of two frontal and lateral patient specific spine X-ray images according to an embodiment of the invention.

FIG. 3 shows an example of two frontal and lateral patient specific spine X-ray images according to an embodiment of the invention.

A frontal X-ray image 31 of a patient shows the patient spine 32 in the coronal plane. A lateral X-ray image 33 of a patient shows the patient spine 34 in the sagittal plane.

Figure 4:
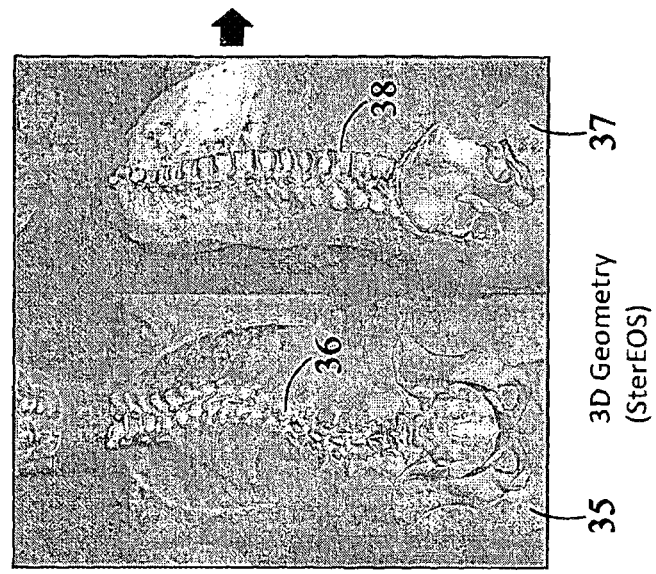
FIG. 4 shows an example of a phase of patient specific 3D geometry modeling according to an embodiment of the invention.

FIG. 4 shows an example of a phase of patient specific 3D geometry modeling according to an embodiment of the invention.

A patient specific 3D geometry modeling is made from both patient specific frontal X-ray image 31 and patient specific lateral X-ray image 33. A projection 36 in coronal plane of this patient specific 3D geometry modeling is shown superposed to the frontal X-ray image 35. A projection 38 in sagittal plane of this patient specific 3D geometry modeling is shown superposed to the lateral X-ray image 37. This patient specific 3D geometry modeling is made from both patient specific frontal X-ray image 31 and patient specific lateral X-ray image 33, for example by using a patient specific 3D geometry modeling or even a patient avatar.

Figure 5:
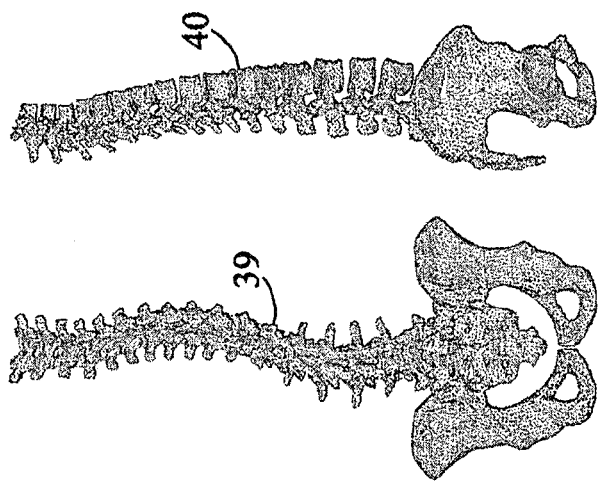
FIG. 5 shows an example of a phase of patient specific 3D finite element modeling according to an embodiment of the invention.

FIG. 5 shows an example of a phase of patient specific 3D finite element modeling according to an embodiment of the invention.

A first patient specific 3D finite element model is made from the patient specific 3D geometry modeling. A frontal view 39 of this patient specific 3D finite element modeling is shown next to a lateral view 40 of this patient specific 3D finite element modeling. This first patient specific 3D finite element model allows two different types of computing: either computing the forces occurring in the patient spine when the patient spine deforms itself, or computing the deformations of the patient spine when external forces are applied on this patient spine.

Figure 6:
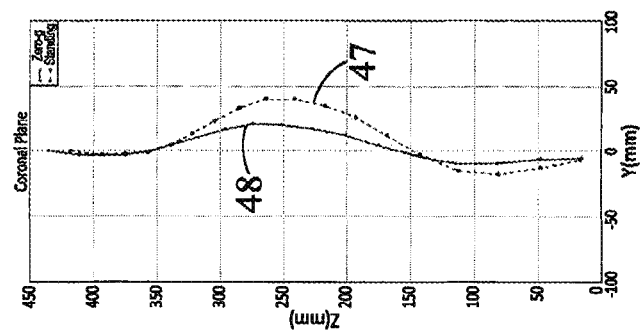
FIG. 6 shows schematically an example of an operation of subtraction of simulated gravitational forces, from a first patient specific spine 3D finite element model to a second patient specific spine 3D finite element model, according to an embodiment of the invention.

FIG. 6 shows schematically an example of an operation of subtraction of simulated gravitational forces, from a first patient specific spine 3D finite element model to a second patient specific spine 3D finite element model, according to an embodiment of the invention.

A second patient specific 3D finite element model is made from the first patient specific 3D finite element model, by subtracting the gravitational forces by simulation. This gravitational forces subtraction simulation tends to extend patient spine as if pulling on it in an upward direction. This gravitational forces subtraction simulation applied on frontal view 41 of this first patient specific 3D finite element modeling is shown by the arrows 42. This gravitational forces subtraction simulation applied on lateral view 43 of this first patient specific 3D finite element modeling is shown by the arrows 44. First patient specific 3D finite element modeling corresponds to a standing patient which is the position of the patient when the X-ray images are taken. Second patient specific 3D finite element modeling corresponds to a lying patient which is the position of the patient when the surgery to cure patient spine scoliosis is performed.

Figure 7A:
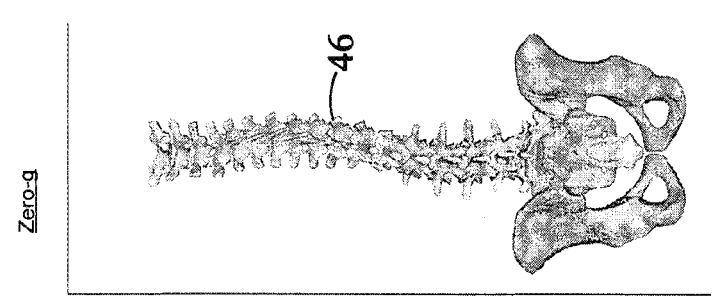
FIGS. 7A & 7B show comparative examples of patient specific spine frontal views of the second patient specific spine 3D finite element model, respectively before and after an operation of subtraction of simulated gravitational forces as shown in FIG. 6, according to an embodiment of the invention.
Figure 7B:
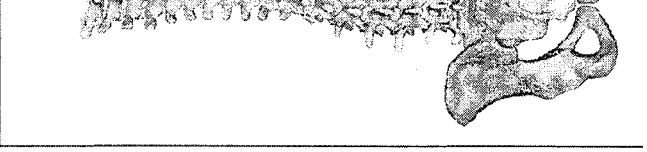

FIGS. 7A & 7B show comparative examples of patient specific spine frontal views of the second patient specific spine 3D finite element model, respectively before and after an operation of subtraction of simulated gravitational forces as shown in FIG. 6, according to an embodiment of the invention.

The frontal view 46 of the second patient specific spine 3D finite element model after the operation of subtraction of simulated gravitational forces shows a patient spine which is less curved and which extends higher than the frontal view 45 of the second patient specific spine 3D finite element model after the operation of subtraction of simulated gravitational forces.

Figure 7C:
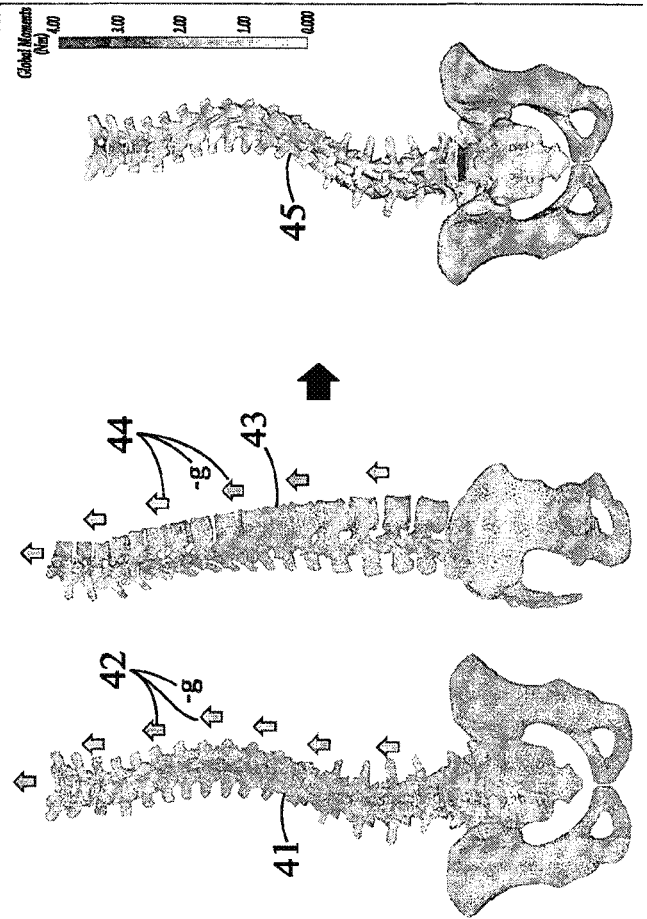
FIG. 7C shows the result of the comparison between comparative examples of patient specific spine frontal views of the second patient specific spine 3D finite element model as shown in FIGS. 7A & 7B, according to an embodiment of the invention.

FIG. 7C shows the result of the comparison between comparative examples of patient specific spine frontal views of the second patient specific spine 3D finite element model as shown in FIGS. 7A & 7B, according to an embodiment of the invention.

The patient spine profile 48 after simulation of subtraction of gravitational forces is already much closer to ideal vertical patient spine in coronal plane than the patient spine profile 47 before simulation of subtraction of gravitational forces. This means that the deformation undergone by the lying patient spine will be more limited than the deformation which would be undergone by the standing patient, when the spinal correction rod implant is implanted.

FIG. 8A shows a comparison between examples of patient specific spine lateral profiles, respectively patient spine profile with scoliosis before surgery, the targeted patient spine profile, and the simulated corrected patient spine profile.

Patient specific spine presents a profile 49 with scoliosis before surgery. To correct this scoliosis, a targeted patient spine profile 50 is scheduled. When implanting spinal correction rod implant to reach this targeted patient spine profile 50, only a corrected patient spine profile 51 can be reached, because of the resistance and of the counter effort of the patient spine. The corrected patient spine profile 51 corrects a good deal of the scoliosis and is notably closer to the targeted patient spine profile 50 than the profile 49 with scoliosis before surgery was, but the residual difference between corrected patient spine profile 51 and targeted patient spine profile 50 is far from being negligible.

FIG. 8B shows schematically a lateral view of an example of a targeted patient spine profile represented with the springs model.

Between the targeted patient spine profile 53 and the patient spine 52 with scoliosis before surgery, virtual horizontal springs 54, vertically regularly spaced from one another, are implemented, each virtual spring 54 joining the middle of a vertebra of the patient spine 52 with scoliosis before surgery and a corresponding point of the targeted patient spine profile 53. The virtual springs 54 exert on patient spine a force Fspring which tends to deform the patient spine so as to become closer to the targeted patient spine profile 53, what happens on next FIG. 8C.

FIG. 8C shows schematically a lateral view of an example of a simulated corrected patient spine profile represented with the springs model.

Once the virtual springs have exerted their efforts, the patient spine 56 has been deformed to get closer to the targeted patient spine profile 55, even if there remains a non-negligible difference. During this deformation of the patient spine 56, two points will be checked, first that no vertebra interpenetrates another vertebra, and second that the effort exerted on each vertebra does not exceed a predetermined threshold which would run the risk to damage or even to break such vertebra. The springs model used as a biomechanical model helps making sure more easily that the targeted spinal correction rod implant shape first is attainable as well as physiological and second that the forces required to obtain it are safe.

Figures 9A, 9B:
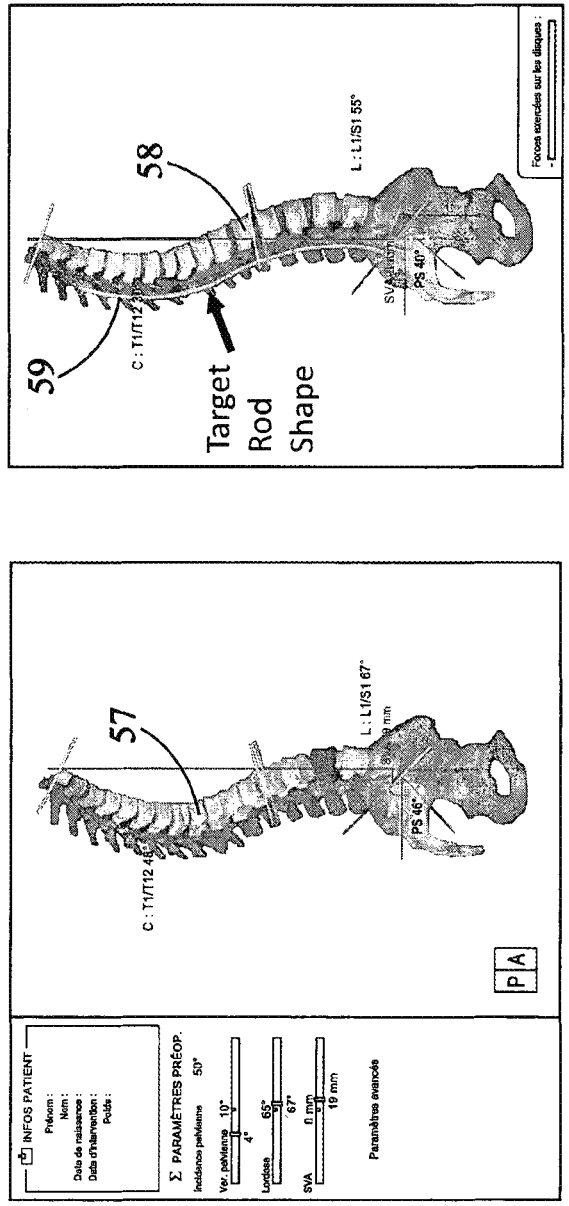
FIG. 9A shows a lateral view of an example of a 3D representation of a patient spine with scoliosis before surgery.
FIG. 9B shows a lateral view of an example of a 3D representation of a targeted patient spine with the associated targeted spinal correction rod implant shape, corresponding to the patient spine with scoliosis before surgery of FIG. 9A.

FIG. 9A shows a lateral view of an example of a 3D representation of a patient spine with scoliosis before surgery.

This patient spine 57 with scoliosis before surgery presents an excessive kyphosis of 48 degrees, angle between vertebrae T1 and T12, as well as an excessive lordosis of 67 degrees, angle between vertebra L1 and sacral plate S1.

FIG. 9B shows a lateral view of an example of a 3D representation of a targeted patient spine with the associated targeted spinal correction rod implant shape, corresponding to the patient spine with scoliosis before surgery of FIG. 9A.

Once the targeted spinal correction rod implant shape 59 implanted on the targeted patient spine 58, this targeted patient spine 58 would present a reduced kyphosis of 30 degrees, as well as a reduced lordosis of 55 degrees.

FIG. 10A shows a frontal view of an example of a 3D representation of an implanted patient spine with the associated implanted spinal correction rod implant shape.

Two rod implants 62 and 63 are implanted on rear part of the patient spine 61 by being attached on spinal implants 64, which are indeed heads of screws 64 screwed within the patient spine 61.

FIG. 10B shows a lateral view of an example of a 3D representation of an implanted patient spine with the associated implanted spinal correction rod implant shape.

Only one of the two rod implants 62 and 63, here the rod implant 62, can be seen on FIG. 10B, as being implanted on rear part of the patient spine 61 by being attached on spinal implants 64 which in turn are fixed within patient spine 61.

FIG. 11 shows a lateral view of an example of a 3D representation of a spinal correction rod implant shape, after implantation on patient spine. The implanted spinal correction rod implant shape 65, when implanted on patient spine, is simulated. Preferably, this is a 3D implanted spinal correction rod implant shape 65.

FIG. 12 shows a comparison between two lateral views of two spinal correction rod implant shapes, respectively before implantation on patient spine and after implantation on patient spine, here without overbending.

So, the pre-operatively rod implant shape 66, which is here the targeted spinal correction rod implant shape, when implanted on patient spine, when trying and correcting patient spine profile, and when undergoing deformed patient spine counter effort, will result in deformed post-operatively rod implant shape 67 which is different from the pre-operatively rod implant shape 66. One or more simulation loops, preferably iterative simulation loops, will lead to modify the pre-operatively rod implant shape 66, so that when implanted on patient spine, it is the post-operatively rod implant shape 67 that matches the targeted spinal correction rod implant shape.

Figures 13A, 13B:
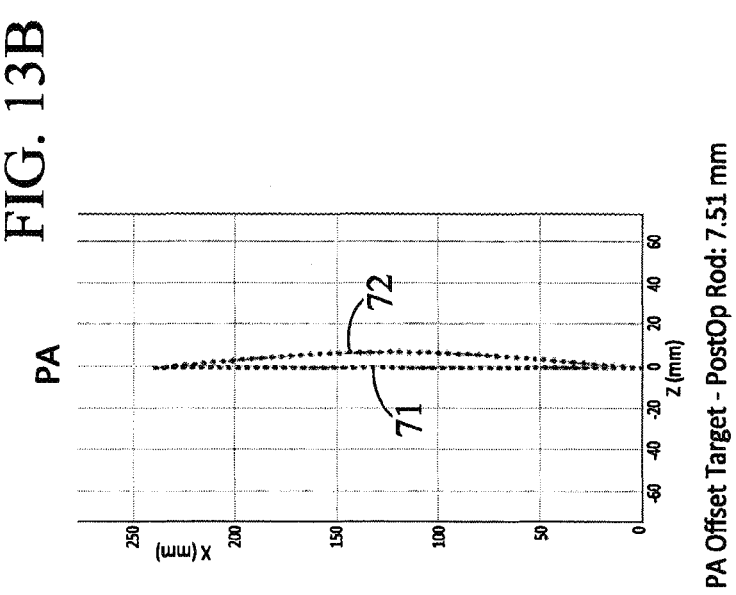
FIG. 13A shows a comparison in sagittal plane between two spinal correction rod implant shapes, respectively targeted spinal correction rod implant shape and implanted spinal correction rod implant shape without previous overbending before implantation on patient spine.
FIG. 13B shows a comparison in coronal plane between two spinal correction rod implant shapes, respectively targeted spinal correction rod implant shape and implanted spinal correction rod implant shape without previous overbending before implantation on patient spine.

FIG. 13A shows a comparison in sagittal plane between two spinal correction rod implant shapes, respectively targeted spinal correction rod implant shape and implanted spinal correction rod implant shape without previous overbending before implantation on patient spine.

In the sagittal plane, the difference between non overbent targeted spinal correction rod implant shape 68 and implanted spinal correction rod implant shape 69 is visible. This difference is to be corrected by the iterative simulation loops so that, after the last simulation loop, targeted spinal correction rod implant shape and implanted spinal correction rod implant shape may become matched as closely as possible, preferably practically superposed, and thereby leading to a balanced implanted spinal correction rod implant shape.

FIG. 13B shows a comparison in coronal plane between two spinal correction rod implant shapes, respectively targeted spinal correction rod implant shape and implanted spinal correction rod implant shape without previous overbending before implantation on patient spine.

In the coronal plane, the difference between non overbent targeted spinal correction rod implant shape 71 and implanted spinal correction rod implant shape 72 is also visible. This difference is to be corrected by the iterative simulation loops so that, after the last simulation loop, targeted spinal correction rod implant shape and implanted spinal correction rod implant shape may become matched as closely as possible, preferably practically superposed, and thereby leading to a straight implanted spinal correction rod implant shape.

Figure 14A:
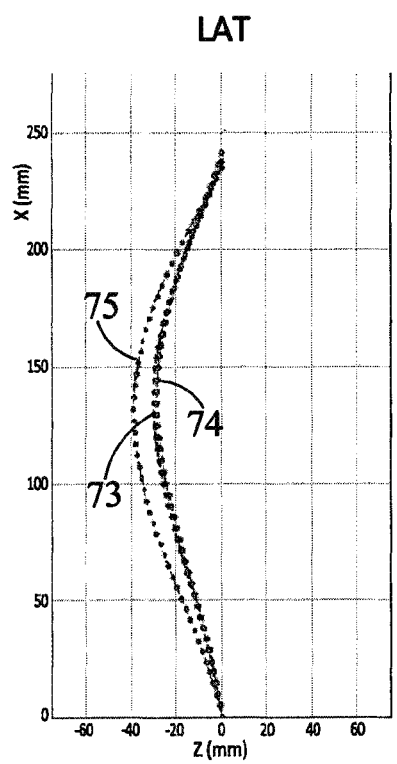
FIG. 14A shows a comparison in sagittal plane between three spinal correction rod implant shapes, respectively targeted spinal correction rod implant shape and implanted spinal correction rod implant shape with previous overbending, as well as overbent spinal correction rod implant shape before implantation on patient spine.

FIG. 14A shows a comparison in sagittal plane between three spinal correction rod implant shapes, respectively targeted spinal correction rod implant shape and implanted spinal correction rod implant shape with previous overbending, as well as overbent spinal correction rod implant shape before implantation on patient spine.

In the sagittal plane, pre-operatively overbent spinal correction rod implant shape 75 is clearly overbent with respect to targeted spinal correction rod implant shape 73, so that, when this pre-operatively overbent spinal correction rod implant shape 75 is implanted on patient spine, then, at the equilibrium, the post-operatively final implanted spinal correction rod implant shape 74 closely matches, here is indeed superposed on, the targeted spinal correction rod implant shape 73, thereby leading to a post-operatively balanced implanted spinal correction rod implant shape 74 in the sagittal plane.

Figure 14B:
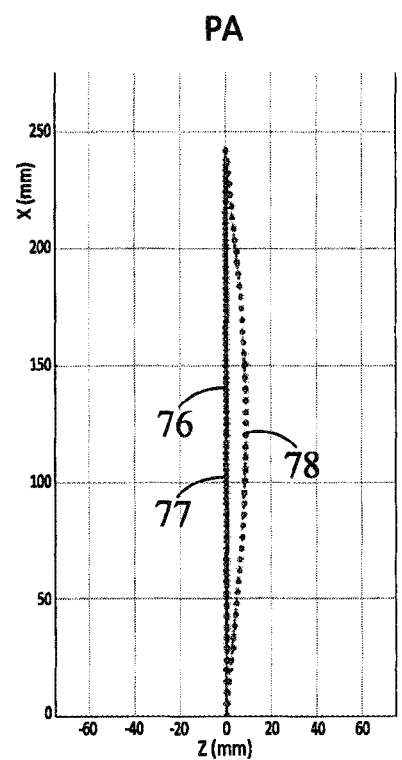
FIG. 14B shows a comparison in coronal plane between three spinal correction rod implant shapes, respectively targeted spinal correction rod implant shape and implanted spinal correction rod implant shape with previous overbending, as well as overbent spinal correction rod implant shape before implantation on patient spine.

FIG. 14B shows a comparison in coronal plane between three spinal correction rod implant shapes, respectively targeted spinal correction rod implant shape and implanted spinal correction rod implant shape with previous overbending, as well as overbent spinal correction rod implant shape before implantation on patient spine.

In the coronal plane, pre-operatively overbent spinal correction rod implant shape 78 is clearly overbent with respect to targeted spinal correction rod implant shape 76, so that, when this pre-operatively overbent spinal correction rod implant shape 78 is implanted on patient spine, then, at the equilibrium, the post-operatively final implanted spinal correction rod implant shape 77 closely matches, here is indeed superposed on, the targeted spinal correction rod implant shape 76, thereby leading to a post-operatively straight implanted spinal correction rod implant shape 76 in the coronal plane.

Figure 15:
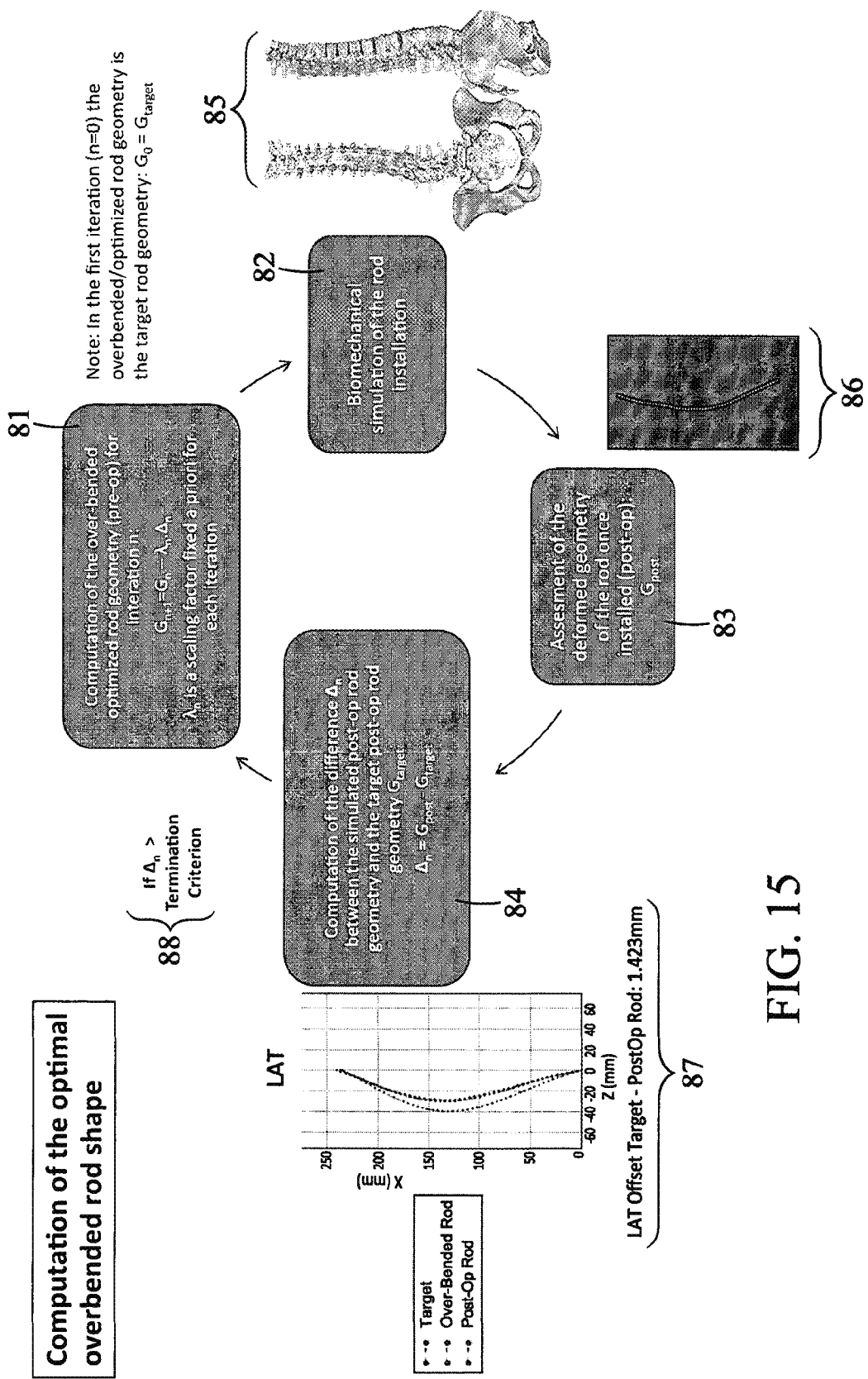
FIG. 15 shows schematically an example of the flow of iterative simulation loops of the spinal correction rod implant manufacturing process part according to an embodiment of the invention.

FIG. 15 shows schematically an example of the flow of iterative simulation loops of the spinal correction rod implant manufacturing process part according to an embodiment of the invention.

An iterative optimization process aiming to find an overbent pre-operative rod's geometry leading post-operative to the target rod's geometry defined in the previous phase. This iterative optimization process can present n iterations which each includes flow of four phases 81 to 84.

A first phase 81 of computation of the pre-operatively overbent spinal correction rod implant shape is performed. For the first simulation loop, this pre-operatively overbent spinal correction rod implant shape is chosen as corresponding to the targeted spinal correction implant rod shape. For subsequent iterative simulation loops, this pre-operatively overbent spinal correction rod implant shape is determined by applying the last overbending representative of the last computed difference at last fourth phase 84 from previous simulation loop to the former pre-operatively overbent spinal correction rod implant shape computed at last first phase 81 from previous simulation loop.

During first phase 81, a computation of the overbent spinal correction rod implant shape's geometry is performed. In the first iteration n=0, the overbent spinal correction rod implant shape's geometry is equal to the targeted spinal correction rod implant shape's geometry: $G_0 = G_{target}$. For iteration n, with n equal or above 1, the overbent spinal correction rod implant shape's geometry is defined according to the equation:

$G_n = G_{n-1} - \lambda_{n-1} \cdot \Delta_{n-1}$, with $G_n$ being the overbent spinal correction rod implant shape's geometry at iteration n, $G_{n-1}$ being the overbent spinal correction rod implant shape's geometry at iteration n−1, being the incremental difference at iteration n between the post-operative simulated spinal correction rod implant shape's geometry and the targeted spinal correction rod implant shape's geometry, $\lambda_n$ being a predetermined scaling factor, for iteration n, preferably identical for all iterations.

A second phase 82 of biomechanical simulation of the spinal correction rod implant installation is performed, thereby simulating the mechanical interaction between pre-operatively spinal correction rod implant and patient spine, thereby leading to a on patient spine spinal correction rod implant implantation 85.

During second phase 82, a biomechanical simulation of the overbent spinal correction rod implant installation is performed. This simulation is done using a personalized biomechanical finite element model of the patient's spine and pelvis, of the spinal implants, screws for instance, and of the rod. The simulation mimics the spinal surgery and, using equations based on the mechanical laws representing mechanical interaction between rod implant and patient spine, computes the deformations and forces exerted on the patient spine and on the rod implants during the surgery.

During second phase 82, the biomechanical model used to mimic the spinal surgery is using a combination of parts of methods already described in the literature for the simulation of the spine surgery, leading to a hybrid model made of rigid non-deformable bodies, for elements like vertebrae, pelvis, spinal implants, and of deformable bodies, for the rod implants. This allows keeping a computational time quite low and having a very good convergence rate. To simulate the attachment of the spinal correction rod implant to the spinal implants, vertebral screws for instance, can be possibly modeled adequately by applying pure displacements or forces. However, preferably, process according to invention uses contact interfaces for such modeling. Contact interfaces, known as such from prior art too, here allow to compute automatically what forces should be exerted on the spinal correction rod implant to insert it into all spinal implants, and to do that while obtaining a very good convergence rate and a very reasonable computational time.

During the 3D finite element simulation, the contact interface, which is a particular type of element aiming at modeling the contact between two bodies, each body being either rigid or deformable, prevents these two bodies from interpenetrating each other by creating "virtual springs" at the nodes where the contact between these two bodies is about to happen. These "virtual springs" create "contact interface forces" that prevent excessive penetration between these two bodies. Ideally, these virtual springs should have an infinite stiffness and enforce absolutely no (0 mm) penetration between these two bodies. However, an infinite stiffness would induce divergence in the iterative resolution process trying to find an equilibrium state by solving the nonlinear equations. Hence, the contact stiffness of the contact interface is therefore adjusted at a finite value which is both sufficiently high but not too high so as to obtain simultaneously a converged solution and an acceptable residual penetration between these two bodies.

A third phase 83 of assessment of the deformed geometry of the pre-operatively spinal correction rod implant when implanted so as to become a post-operatively spinal correction rod implant is performed, thereby leading to an implanted spinal correction rod implant shape 86.

During third phase 83, based on the previously described simulation, a computation of the deformed geometry $G_{post}$ of the overbent spinal correction rod implant shape once installed and balanced, so post-operative, is performed.

A fourth phase 84 of computation of a difference between on the one hand the simulated post-operatively spinal correction rod implant shape and on the other hand the targeted spinal correction rod implant shape is computed, thereby leading to a checking of the match between simulated post-operatively spinal correction rod implant shape and targeted spinal correction rod implant shape so as to decide whether termination condition 88 is met or not. If condition is met, then the post-operatively overbent spinal correction rod implant shape is the last post-operatively overbent spinal correction rod implant shape got at last first phase 81 of last simulation loop. If condition is not met, an additional simulation loop is started again from first phase 81.

During fourth phase 84, in simulation loop n, a computation of the difference $\Delta_n$ between the simulated post-operative spinal correction rod implant shape's geometry and the targeted post-operative spinal correction rod implant shape's geometry $G_{target}$ is performed. So one gets:

$$\Delta_n = G_{post} - G_{target}$$

If $\Delta_n$ is inferior or equal to the termination criterion of the iterative process, preferably predetermined, the iterative process stops and the overbent spinal correction rod implant shape's geometry at iteration n, $G_n$, is considered to be the optimal overbent spinal correction rod implant shape's geometry.

If, on the contrary, $\Delta_n$ is superior to the termination criterion of the iterative process, the iterative process continues and a new iteration n+1 takes place. For this new iteration n+1, the tested overbent spinal correction rod implant shape's geometry will be: $G_{n+1} = G_n - \lambda_n \cdot \Delta_n$, with $\lambda_n$ being a scaling factor of the difference $\Delta_n$, preferably identical for all iterations.

Figure 16:
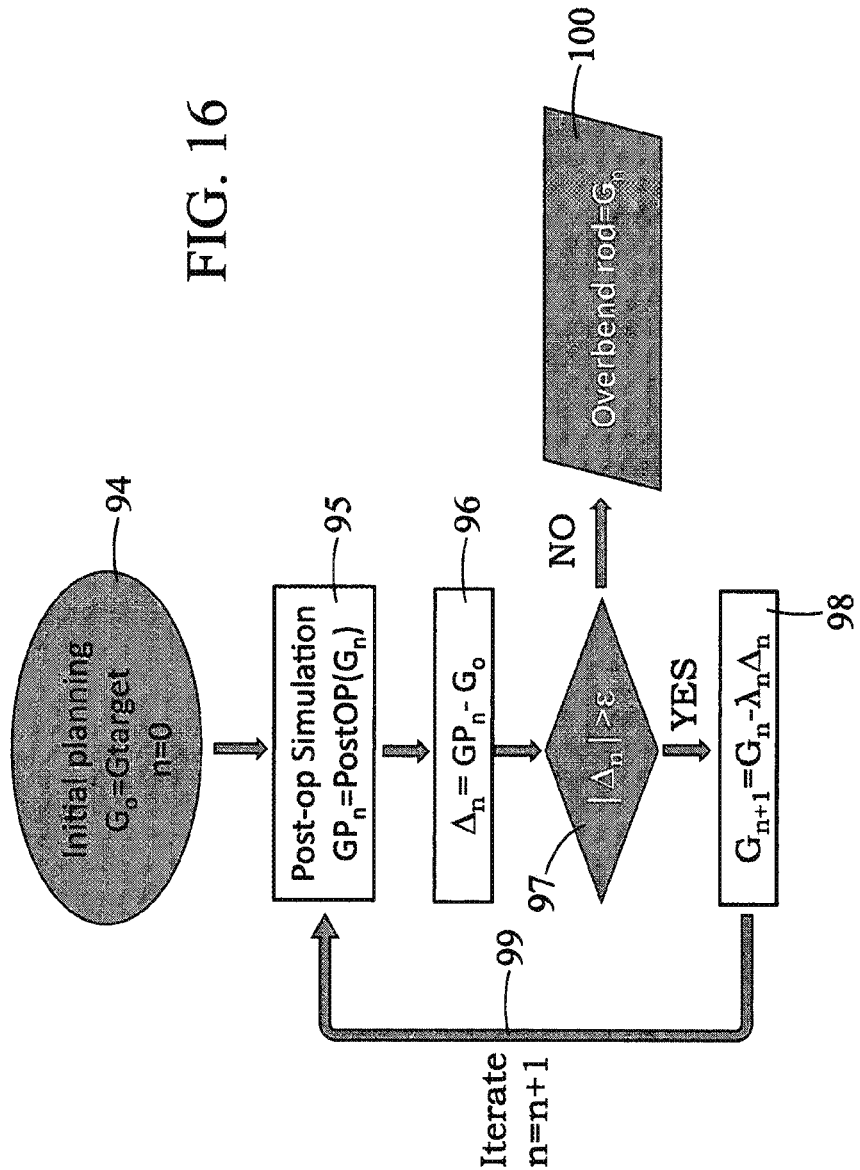
FIG. 16 shows schematically a summary of the calculations performed in the flow of iterative simulation loops of FIG. 15.

FIG. 16 shows schematically a summary of the calculations performed in the flow of iterative simulation loops of FIG. 15.

An initialization phase 94 is performed by taking $G_0 = G_{target}$ for n=0.

Then a post-operative simulation phase 95 is done so as to get:

$GP_n = \text{post-operative}(G_n)$, meaning that the post-operative geometry of the simulated implanted spinal correction rod implant shape is got from the mechanical interaction of the patient spine and of the overbent pre-operative spinal correction rod implant.

Then, there is a difference calculation 96 phase, calculating the difference $\Delta_n$ between the overbent pre-operative spinal correction rod implant shape $GP_n$ and the targeted spinal correction rod implant shape $G_0$, so as to get following equation: $\Delta_n = GP_n - G_0$.

Then, there is a comparison phase 97 of the absolute value of this difference $\Delta_n$ with a predetermined threshold $\varepsilon$. If absolute value of this difference $\Delta_n$ is below said predetermined threshold $\varepsilon$, then the geometry $G_n$ is kept for the overbent spinal correction rod implant shape. If, on the contrary, absolute value of this difference $\Delta_n$ is above said predetermined threshold $\varepsilon$, then there is another iteration of the simulation loop, n becoming n+1, starting again from simulation phase 95.

The invention has been described with reference to preferred embodiments. However, many variations are possible within the scope of the invention.

The invention claimed is:

1. A spinal correction rod implant manufacturing process part comprising:
   estimating a targeted spinal correction rod implant shape which is based on a patient-specific spine shape correction and which includes a patient-specific spine 3D modeling; and
   conducting one or more simulation loops each comprising:
   simulating, in a first simulation step, an intermediate spinal correction rod implant shape resulting from a modeling of a mechanical interaction between said patient-specific spine and one of: (i) for a first simulation loop of the one or more simulation loops, said targeted spinal correction rod implant shape, and (ii) for one or more subsequent simulation loops subsequent to the first simulation loop, an overbent spinal correction rod implant shape resulting from a previous simulation loop, and simulating, in a second simulation step, a spinal correction rod implant shape overbending which is applied to said targeted spinal correction rod implant shape to give a resulting overbent spinal correction rod implant shape and which is representative of a difference between (i) for the first simulation loop when the mechanical interaction is between the patient-specific spine and the first simulation loop, said targeted spinal correction rod implant shape, or for the one or more subsequent simulation loops when the mechanical interaction is between the patient-specific spine and the one or more subsequent simulation loops, said overbent spinal correction rod implant shape resulting from the previous simulation loop, and (ii) said intermediate spinal correction rod implant shape.

2. The spinal correction rod implant manufacturing process part according to claim 1, wherein the one or more simulation loops comprise only a single simulation loop.

3. The spinal correction rod implant manufacturing process part according to claim 1, wherein the at least two simulation loops comprise
at least 2 iterative simulation loops, preferably at least 5 iterative simulation loops, more preferably less than 10 iterative simulation loops.

4. The spinal correction rod implant manufacturing process part according to claim 3, wherein:
the number of iterative simulation loops is determined during running of simulation loops by checking, at each of the simulation loops, that the difference between targeted spinal correction rod implant shape and intermediate spinal correction rod implant shape is below a predetermined threshold.

5. The spinal correction rod implant manufacturing process part according to claim 3, wherein the number of iterative simulation loops is a predetermined number of iterative simulation loops, and
wherein said predetermined number of iterative simulation loops depends on one or more of: (i) the type of patient spine scoliosis and (ii) the magnitude of patient spine scoliosis.

6. The spinal correction rod implant manufacturing process part according to claim 1, wherein:
said mechanical interaction modeling is selected or structured so that, when resulting overbent spinal correction rod implant is to be implanted on said patient-specific spine and when said implanted overbent spinal correction rod implant shape is to be modified by an effective mechanical interaction between said implanted overbent spinal correction rod implant shape and said patient specific spine to become an implanted final spinal correction rod implant shape, said implanted final spinal correction rod implant shape is closer to said targeted spinal correction rod implant shape than said intermediate spinal correction rod implant shape from the first simulation loop.

7. The spinal correction rod implant manufacturing process part according to claim 6, wherein:
said implanted final spinal correction rod implant shape is closer to said targeted spinal correction rod implant shape than said intermediate spinal correction rod implant shape, by at least a factor 2, preferably by at least a factor 5, more preferably by at least a factor 10.

8. The spinal correction rod implant manufacturing process part according to claim 1, wherein:
in said second simulation step, said spinal correction rod implant shape overbending in sagittal plane is the difference between (i) for the first simulation loop, said targeted spinal correction rod implant shape projection in sagittal plane, or, for the subsequent simulation loops, an overbent spinal correction rod implant shape resulting from the previous loop projection in sagittal plane, and (ii) said intermediate spinal correction rod implant shape projection in sagittal plane.

9. The spinal correction rod implant manufacturing process part according to claim 1, wherein:
in said second simulation step, said spinal correction rod implant shape overbending in coronal plane is the difference between (i) for the first simulation loop, said targeted spinal correction rod implant shape projection in coronal plane, or, for the subsequent simulation loops, an overbent spinal correction rod implant shape resulting from the previous loop projection in coronal plane, and (ii) said intermediate spinal correction rod implant shape projection in coronal plane.

10. The spinal correction rod implant manufacturing process part according to claim 1, wherein:
in said first simulation step, said mechanical interaction modeling uses, as input parameters, at least both the patient specific spine rigidity before correction and the distances existing between said targeted spinal correction rod implant shape and said patient specific spine before correction.

11. The spinal correction rod implant manufacturing process part according to claim 1, wherein:
in said first simulation step, said mechanical interaction modeling uses, as input parameters, at least both the spinal correction rod implant material and the spinal correction rod implant section.

12. The spinal correction rod implant manufacturing process part according to claim 1, wherein:
in said first simulation step, said mechanical interaction modeling is based on hybrid model integrating:
rigid non-deformable bodies both for patient spine vertebrae and for spinal support implants attached on patient spine vertebrae and supporting one or more spinal correction rod implants, and
one or more deformable bodies for said one or more spinal correction rod implant.

13. The spinal correction rod implant manufacturing process part according to claim 12, wherein:
said hybrid model also integrates contact interfaces respectively located between rigid non-deformable bodies of spinal support implants and a deformable body of said spinal correction rod implant.

14. The spinal correction rod implant manufacturing process part according to claim 12, wherein:
said contact interfaces include virtual springs at nodes where the contact between said two bodies is about to happen, the stiffness of said virtual springs being chosen sufficiently high to get only a residual penetration between said two bodies and not too high to get a high convergence rate in the iterative resolution process.

15. The spinal correction rod implant manufacturing process part according to claim 1, further comprising, after completion of the last second simulation step, a supplementary check step including:

simulated implanting said resulting overbent spinal correction rod implant on said patient specific spine to give an implanted overbent spinal correction rod implant shape, modifying said implanted overbent spinal correction rod implant shape by a simulated mechanical interaction between said implanted overbent spinal correction rod implant shape and said patient specific spine to give an implanted final spinal correction rod implant shape, comparing a first difference between said implanted final spinal correction rod implant shape and said targeted spinal correction rod implant shape with a second difference between said intermediate spinal correction rod implant shape and said targeted spinal correction rod implant shape, and validation checking that said implanted final spinal correction rod implant shape is closer to said targeted spinal correction rod implant shape than said intermediate spinal correction rod implant shape, preferably by at least a factor 2, more preferably by at least a factor 5, even more preferably by at least a factor 10.

16. The spinal correction rod implant manufacturing process part according to claim 1, wherein said estimating comprises:
patient-specific spine 3D geometry modeling performed at the beginning of said estimating.

17. The spinal correction rod implant manufacturing process part according to claim 16, wherein said 3D geometry modeling comprises:
taking both a frontal patient-specific spine X-ray image and a lateral patient-specific spine X-ray image,
generating a patient-specific spine 3D geometry model from both said frontal and lateral patient specific spine X-ray images.

18. The spinal correction rod implant manufacturing process part according to claim 1, wherein said estimating comprises:
patient-specific spine 3D finite element modeling performed in the middle of said estimating.

19. The spinal correction rod implant manufacturing process part according to claim 18, wherein said 3D finite element modeling comprises:
subtracting simulated gravitational forces, from a first patient-specific spine 3D finite element model, representative of patient spine in a vertical image taking position, to obtain a second patient-specific spine 3D finite element model, representative of a patient spine in horizontal surgery performing position.

20. The spinal correction rod implant manufacturing process part according to claim 19, wherein:
said first patient-specific spine 3D finite element model comes from a patient-specific spine 3D geometry model.

21. The spinal correction rod implant manufacturing process part according to claim 18, wherein:
in said 3D finite element modeling, said 3D finite element modeling of said patient-specific spine includes one or more interbody cages and/or one or more osteotomies.

22. The spinal correction rod implant manufacturing process part according to claim 1, wherein said estimating comprises:
patient-specific spine correction feasibility assessing performed at the end of said estimating.

23. The spinal correction rod implant manufacturing process part according to claim 22, wherein said correction feasibility assessing comprises:
comparing said second patient-specific spine 3D finite element model and an ideally aimed corrected patient spine, to obtain a patient-specific spine shape correction and a corresponding targeted spinal correction rod implant,
feasibility checking said patient-specific spine shape correction, including one or more of:
(i) checking biomechanical feasibility, at least by checking that vertebrae of the patient specific spine do not interfere with one another when said targeted spinal correction rod implant will be implanted on said patient-specific spine, and
(ii) checking correction feasibility, at least by checking that the corrective forces, exerted when said targeted spinal correction rod implant will be implanted on said patient specific spine, do not exceed a predetermined threshold above which the risk of damage or even of break of a vertebra of the patient specific spine becomes non-negligible.

24. The spinal correction rod implant manufacturing process part according to claim 23, wherein:
said feasibility checking of said patient-specific spine shape correction is based on an essentially linear representation of the efforts exerted by said patient-specific spine on said targeted spinal correction rod implant.

25. The spinal correction rod implant manufacturing process part according to claim 24, wherein:
said essentially linear representation of the efforts exerted by said patient-specific spine on said targeted spinal correction rod implant is based on a springs model.

26. The spinal correction rod implant manufacturing process part according to claim 25, wherein:
in said springs model, each tensional spring has a first extremity which is attached to the center of a vertebra of the patient-specific spine and a second extremity which is attached to the corresponding position of the targeted spinal correction rod implant shape.

27. The spinal correction rod implant manufacturing process part according to claim 26, wherein:
different existing offsets between vertebrae to be corrected in the patient-specific spine, are cancelled so that the initial force applied by the tensional springs on all the vertebrae to be corrected is the same.

28. The spinal correction rod implant manufacturing process part according to claim 26, wherein:
additional torsional springs are implemented between said targeted spinal correction rod implant shape and said patient-specific spine shape to correct the axial rotation of the vertebrae of the patient-specific spine in the transverse plane with respect to the patient-specific spine.

29. The spinal correction rod implant manufacturing process part according to claim 28, wherein:
different existing offsets between vertebrae to be corrected in the patient specific spine are cancelled so that the initial moment applied by the torsional springs on all the vertebrae to be corrected is the same.

30. The spinal correction rod implant manufacturing process part according to claim 1, wherein:
said mechanical interaction modeling uses a stiffness matrix for each intervertebral unit needing a spinal correction in the patient-specific spine.

31. A spinal correction rod implant manufacturing process part comprising:
estimating a targeted spinal correction rod implant shape which is based on a patient-specific spine shape correction and which includes a patient-specific spine 3D modeling; and conducting at least two simulation loops each comprising:
  simulating, in a first simulation step, an intermediate spinal correction rod implant shape resulting from a modeling of a mechanical interaction between said patient-specific spine and one of: (i) for a first simulation loop of the one or more simulation loops, said targeted spinal correction rod implant shape, and (ii) for one or more subsequent simulation loops subsequent to the first simulation loop, an overbent spinal correction rod implant shape resulting from a previous simulation loop, and
  simulating, in a second simulation step, a spinal correction rod implant shape overbending which is applied to said targeted spinal correction rod implant shape to give a resulting overbent spinal correction rod implant shape and which is representative of a difference between (i) for the first simulation loop when the mechanical interaction is between the patient-specific spine and the first simulation loop, said targeted spinal correction rod implant shape, or for the one or more subsequent simulation loops when the mechanical interaction is between the patient-specific spine and the one or more subsequent simulation loops, said overbent spinal correction rod implant shape resulting from the previous simulation loop, and (ii) said intermediate spinal correction rod implant shape.

* * * * *